United States Patent [19]

Ruff et al.

[11] Patent Number: 5,994,589
[45] Date of Patent: Nov. 30, 1999

[54] PROCESS FOR PREPARING 2,5,6-TRIMETHYL-2-CYCLOHEXEN-1-ONE

[75] Inventors: Detlef Ruff, Ludwigshafen; Wolfram Burst, Mannheim; Wulf Kaiser, Bad Dürkheim; Manfred Stroezel, Ilvesheim, all of Germany

[73] Assignee: BASF Aktiengesellschaft, Ludwigshafen, Germany

[21] Appl. No.: 09/265,695

[22] Filed: Mar. 10, 1999

[30] Foreign Application Priority Data

Mar. 12, 1998 [DE] Germany ............... 198 10 671

[51] Int. Cl.⁶ .................................. C07C 45/75
[52] U.S. Cl. ............... 568/345; 568/349; 568/361
[58] Field of Search .................... 568/345, 347, 568/349, 361

[56] References Cited

U.S. PATENT DOCUMENTS

| | | | |
|---|---|---|---|
| 3,857,892 | 12/1974 | Wehrli | 260/586 R |
| 4,128,728 | 12/1978 | Arnold et al. | 566/799 |
| 4,820,874 | 4/1989 | Tavs | 568/350 |

FOREIGN PATENT DOCUMENTS 852 935  11/1960  United Kingdom.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process for preparing 2,5,6-trimethyl-2-cyclohexen-1-one by reacting diethyl ketone with crotonaldehyde or a compound which is converted under the chosen reaction conditions into crotonaldehyde, in the presence of basic agents at elevated temperature, which comprises a) simultaneously pumping one mole of crotonaldehyde or one mole of a compound which is converted under the reaction conditions into crotonaldehyde, about 5 to 30 moles of diethyl ketone and the aqueous solution or suspension of a strong base, through separate lines or at least partly in the form of a suitable mixture, continuously into a pressure vessel, which is heated where appropriate and which ensures vigorous mixing, in such a way that b) the reaction temperature is between 150° C. and 350° C., and the average residence time in the pressure vessel is only about 0.1 second to 20 minutes.

7 Claims, No Drawings

PROCESS FOR PREPARING 2,5,6-TRIMETHYL-2-CYCLOHEXEN-1-ONE

The invention relates to an improved process for preparing 2,5,6-trimethyl-2-cyclohexen-1-one. The product of the process is of great industrial importance because it can easily be dehydrogenated industrially to 2,3,6-trimethylphenol which is an important precursor for synthesizing vitamin E.

DE 1 793 037 discloses a process for preparing 2,5,6-trimethyl-2-cyclohexen-1-one by reacting diethyl ketone with crotonaldehyde or a compound which is converted under the chosen reaction conditions in crotonaldehyde, in the presence of basic compounds, subsequently neutralizing the reaction mixture and working it up by distillation. The finding of this simple possibility for preparing trimethylcyclohexenone and thus trimethylphenol was at that time an enormous improvement in the synthetic preparation of vitamin E, because up till then it was possible to prepare trimethylphenol only by the difficult and unselective alkylation of phenol. However, the yields of this process, which is very good per se, are still unsatisfactory; as demonstrated by the examples, they are between 40% and 77%. Another disadvantage of this process is that to date it has been possible to operate it only batchwise, which for preparation on a large scale leads to very large reaction vessels and thus very small space-time yields. Since this reaction with α,β-unsaturated aldehydes must always be carried out in high dilution, very large amounts of boiling solvents are in continuous use, which is undesirable for safety reasons.

DE 3 636 057 describes a process for preparing 2,5,6-trimethyl-2-cyclohexen-1-one in which the yields which can be achieved in accordance with DE 1 793 037 can be improved by heating the distillation residues resulting from the workup by distillation, where appropriate in the presence of catalytic amounts of alkali, at temperatures from 120 to 250° C.

In addition, JP 58-035141 A2 describes a process for preparing 2-cyclohexen-1-ones by reacting α,β-unsaturated aldehydes with aliphatic ketones in the gas phase. The advantage compared with reaction in the liquid phase is stated to be suppression of the polymerization of the α,β-unsaturated aldehydes, such as acrolein or crotonaldehyde. However, the yields of 2,5,6-trimethyl-2-cyclohexen-1-one achieved in the appropriate examples of the reaction of crotonaldehyde are again only between 57 and 76% of theory.

The reaction described in DE 1 793 037 has also up till now been operated on an industrial scale as a batchwise process in which crotonaldehyde was added dropwise to a mixture of diethyl ketone, base and, where appropriate, a solvent, it having been regarded as advantageous for the crotonaldehyde or its precursor to be diluted by a solvent before the dropwise addition. To complete the reaction after the end of the addition of crotonaldehyde, the reaction mixture was heated further for a certain time.

It was thought not to be possible to carry out the process continuously because it was to be expected that if the process was carried out continuously most of the crotonaldehyde would undergo side reactions through self-polymerization due to its high concentration in the reaction mixture. It would also have been expected that a whole cascade of reactors would be necessary to ensure an after-reaction time.

The best way of carrying out the reaction to date provides reaction times of one hour. The condensation is generally carried out at temperatures between –20° C. and 200° C., preferably between 20 and 120° C. (cf. DE 1 793 037, Example 1). It was really to be expected that the reaction mixture would resinify because of secondary reactions through heat treatment beyond the range described.

DE 3 636 057 describes that the maximum limiting temperature for treatment of the reaction discharge is 220° C. and that treatment up to 250° C. is possible only on addition of inert high boilers.

It was thus to be expected that at temperatures higher than those described to date there would be complete polymerization of the α,β-unsaturated aldehyde or of the entire reaction discharge.

It is an object of the present invention to find conditions under which it is possible to prepare 2,5,6-trimethyl-2-cyclohexen-1-one by reacting diethyl ketone with crotonaldehyde on the industrial scale with better yields and better space-time yields. This meant in practice to find conditions under which said reaction can be carried out continuously, and this if possible with improvement of the chemical yield and the quality of the 2,5,6-trimethyl-2-cyclohexen-1-one.

We have found that this object is achieved since it is possible and very advantageous to carry out the reaction of diethyl ketone with crotonaldehyde in the presence of bases continuously when excess diethyl ketone, the crotonaldehyde and the solution or suspension of a strong base are pumped simultaneously and continuously into a pressure vessel which is heated where appropriate and has vigorous mixing in such a way that the reaction temperature is between 150 and 350° C. and the average residence time in the pressure vessel is only about 0.1 second to 60 seconds.

It has also been found, surprisingly, that when particularly suitable residence times are maintained when carrying out the reaction continuously it is possible to dispense with predilution of the crotonaldehyde with inert high boilers, and that the continuous synthesis can be carried out in a single reaction vessel. This means that the use of several reaction vessels arranged in series is unnecessary. It has further emerged that when the process is carried out continuously it is in fact possible to reduce considerably the amount of high-boiling by-products by suitable choice of the residence time.

The invention therefore relates to a process for preparing 2,5,6-trimethyl-2-cyclohexen-1-one by reacting diethyl ketone with crotonaldehyde or a compound which is converted under the chosen reaction conditions into crotonaldehyde, in the presence of basic agents at elevated temperature, which comprises a) simultaneously pumping one mole of crotonaldehyde or one mole of a compound which is converted under the reaction conditions into crotonaldehyde, about 5 to 30 moles of diethyl ketone and the solution or suspension of a strong base, through separate lines or at least partly in the form of a mixture, continuously into a pressure vessel, which is heated where appropriate and which ensures vigorous mixing, in such a way that b) the reaction temperature is between 150° C. and 350° C., and the average residence time in the pressure vessel is only about 0.1 second to 20 minutes, preferably 0.1 second to 15 minutes, in particular 0.1 second to 60 seconds.

The advantageous procedure for the process according to the invention is simultaneously to pump the crotonaldehyde, the diethyl ketone and the solution of the strong base into the pressure vessel in such a way that the reaction temperature is 200 to 300° C., preferably 220 to 290° C., in particular 225 to 280° C. It is possible in this case to heat the pressure vessel itself and to introduce the reaction components without previous heating. However, the energy necessary for the reaction can also be introduced into the reaction vessel at least partly by preheating the reaction components.

To carry out the process according to the invention, it is possible to introduce the 3 reaction components, the crotonaldehyde or the compound which is converted into crotonaldehyde under the reaction conditions, the diethyl ketone and the solution of the strong base, simultaneously but through separate lines into the pressure vessel. However, it is also possible to introduce the reaction components at least partly in the form of a mixture into the pressure vessel if care is taken that the crotonaldehyde, which is well known to be prone to polymerization in an alkaline medium, does not come into contact with the solution or suspension of the strong base before the reaction. Thus, for example, a mixture of crotonaldehyde and diethyl ketone can be introduced through one line and the solution of the base can be introduced through another line. However, the diethyl ketone and the solution of the base can also be mixed to form an emulsion, and the latter can be introduced through one line, and the crotonaldehyde can be introduced through a second line. Depending on the design of the reaction systems, it may be expedient to introduce the crotonaldehyde mixed with part of the diethyl ketone, to introduce the solution of the base through a second line and to introduce the remainder of the diethyl ketone, preheated, through a third line into the pressure vessel.

The diethyl ketone is generally used in amounts of about 5 to 30 mol, preferably 10 to 20 mol, per mole of crotonaldehyde or per mole of a compound which is converted into crotonaldehyde under the reaction conditions. Although diethyl ketone can also be employed in even larger amounts, this has no advantages and, on the contrary, only makes the workup of the reaction mixture unnecessarily difficult and unnecessarily increases the energy costs for the workup by distillation.

Strongly basic agents which can be used in the process according to the invention are hydroxides, oxides, alcoholates, amides, hydrides, carbonates or organometallic compounds of the alkali metals or alkaline earth metals or quaternary ammonium hydroxides. Examples which may be mentioned are: sodium, potassium or calcium hydroxide, sodium carbonate, potassium carbonate, sodium methoxide, sodamide, sodium hydride, phenyllithium, methyllithium and tetramethylammonium hydroxide. It is generally advantageous for the strong base to be introduced in the form of a solution or a suspension into the reaction vessel.

It is advantageous to carry out the process according to the invention using alkali metal alcoholates in the corresponding alkanols, or else alkali metal hydroxides in aqueous solution, as the strong bases. The use of aqueous solutions has the great advantage that the process is terminated by the separation of the phases when the vigorous mixing is stopped, without neutralization being necessary.

It is therefore particularly advantageous to use a concentrated aqueous solution of an alkali metal hydroxide, in particular KOH, i.e. an aqueous solution of the alkali metal hydroxide, in particular of potassium hydroxide, in which the alkali metal hydroxide, in particular the KOH, is present in a concentration of about 30 to about 70% by weight. If more highly concentrated aqueous solutions were used, heated lines and pumps would be necessary. It is expedient to use the concentrated aqueous solution of KOH which is about 48 to 50% by weight and is commercially available.

The strong base is generally used in amounts of from 0.02 to 3 mol per mole of crotonaldehyde. The amount of the strong base depends substantially on the vigorousness of the mixing in the pressure vessel.

The reaction according to the invention is generally carried out in a pressure range which is somewhat above the autogenous pressure of the reaction mixture, i.e. at a pressure in the range where the reaction components are liquid at the given temperature and boiling is prevented.

The reaction mixture can be worked up as described in DE 1 793 037.

It is possible by means of the process according to the invention to prepare 2,5,6-trimethyl-2-cyclohexen-1-one, which is an essential intermediate for preparing vitamin E, in a technically straightforward manner in very good yields and very good space-time yields also on the industrial scale.

EXAMPLES 1–3

A mixture of in each case one mole of crotonaldehyde and 16 moles of diethyl ketone was pumped continuously into a pressure vessel with vigorous mixing in such a way that the reaction temperature and the average residence time had the values evident from Table 1. At the same time, through a separate feed, in each case the number of moles of KOH per mole of crotonaldehyde which is evident from Table 1 were metered in the form of a concentrated aqueous solution into this pressure vessel with vigorous mixing. The system was set at a pressure above the autogenous pressure of the reaction mixture via a discharge valve. The discharge from the reaction was cooled to room temperature (RT). The yield was determined by gas chromatography with an internal standard (GC). The yield of 2,5,6-trimethyl-2-cyclohexen-1-one, based on crotonaldehyde, obtained in each case is indicated in the table below.

TABLE

| Example | Reaction temperature [°C.] | Residence time | Amount KOH [mol] | Yield [% of theory] |
|---|---|---|---|---|
| 1 | 237 | 10 min | 0.3 | 78 |
| 2 | 277 | 10 min | 0.3 | 82 |
| 3 | 269 | 2 min | 0.3 | 83 |
| 4 | 242 | 5 sec | 0.2 | 86 |
| 5 | 268 | 5 sec | 0.2 | 92 |

We claim:
1. A continuous process for preparing 2,5,6-trimethyl-2-cyclohexen-1-one by reacting diethyl ketone with crotonaldehyde or a compound which is converted under the here specified reaction conditions into crotonaldehyde, in the presence of basic agents at elevated temperature, which comprises
   a) simultaneously pumping one mole of crotonaldehyde or one mole of a compound which is converted under the reaction conditions into crotonaldehyde, about 5 to 30 moles of, diethyl ketone and an aqueous solution or suspension of a strong base, through separate lines or at least partly in the form of a mixture of the reactants, continuously into a pressure vessel, which is heated where appropriate and which ensures a vigorous mixing, and continuously discharging the resulting mixture in such a way that
   b) the reaction temperature is between 150° C. and 350° C., and the average residence time in the pressure vessel is only about 0.1 second to 20 minutes.
2. A process as claimed in claim 1, wherein the crotonaldehyde, the diethyl ketone and the solution or suspension of the strong base are pumped simultaneously into the pressure vessel in such a way that the reaction temperature is 200 to 300° C.

3. A process as claimed in claim 1, wherein the crotonaldehyde, the diethyl ketone and the solution of the strong base are pumped simultaneously into the pressure vessel in such a way that the reaction temperature is 220 to 290° C.

4. A process as claimed in claim 1, wherein the crotonaldehyde, the diethyl ketone and the solution of the strong base are pumped simultaneously into the pressure vessel in such a way that the reaction temperature is 225 to 280° C.

5. A process as claimed in claim 1, wherein the residence time in the pressure vessel is about 0.1 second to 60 seconds.

6. A process as claimed in claim 1, wherein concentrated aqueous potassium hydroxide solution is used as the solution of a strong base.

7. A process as claimed in claim 1, wherein about 0.02 to 3 mol of a strong base are used.

* * * * *